(12) United States Patent
Cardot et al.

(10) Patent No.: US 7,442,315 B2
(45) Date of Patent: Oct. 28, 2008

(54) SEPARATION DEVICE COMPRISING A SEPARATION CHANNEL AND A COUNTER-CHANNEL

(75) Inventors: Philippe Cardot, Limoges (FR); Serge Battu, Limoges (FR); Robert Sarrazin, Verneuil sur Vienne (FR)

(73) Assignee: Universite de Limoges, Limoges (FR)

( * ) Notice: Subject to any disclaimer, the term of this patent is extended or adjusted under 35 U.S.C. 154(b) by 665 days.

(21) Appl. No.: 11/159,142

(22) Filed: Jun. 23, 2005

(65) Prior Publication Data

US 2006/0151403 A1    Jul. 13, 2006

(30) Foreign Application Priority Data

Jan. 7, 2005   (FR) ................... 05 00151

(51) Int. Cl.
*B01D 1/04* (2006.01)
(52) U.S. Cl. .............. 210/782; 210/781; 210/360.1; 210/360.2; 210/380.1; 494/45; 494/85
(58) Field of Classification Search ........ 210/781, 210/782, 360.1, 360.2, 380.1; 494/45, 85
See application file for complete search history.

(56) References Cited

U.S. PATENT DOCUMENTS

| 3,175,762 A | 3/1965 | Dinter, Jr. |
| 4,284,498 A * | 8/1981 | Grant et al. ............. 209/155 |
| 4,353,795 A | 10/1982 | Romanauskas |
| 4,743,227 A | 5/1988 | Takeuchi |

FOREIGN PATENT DOCUMENTS

EP    0 230 899    8/1987

* cited by examiner

*Primary Examiner*—David A Reifsnyder
(74) *Attorney, Agent, or Firm*—McLeland Patent Law Office, P.L.L.C.

(57) ABSTRACT

The present invention relates to a separation device notably for a flow-force fractionation of suspended substances in a liquid carrier, said separation device comprising a separation channel and a counter-channel.

The object of the present invention is mainly the separation of living cells, preferably of human origin, in particular cells which are found in body fluids.

28 Claims, 5 Drawing Sheets

SEPARATION DEVICE COMPRISING A SEPARATION CHANNEL AND A COUNTER-CHANNEL

The invention relates to a device for separating solutions containing suspended substances in a liquid carrier, advantageously used as a separation bowl in a centrifuge, preferably by a flow-force coupling fractionation technique (FFF).

STATE OF THE ART

In the state of the art, as for example from U.S. Pat. No. 4,743,227, it is known that the separation of solutions containing suspended substances in a liquid carrier may be carried out by a separation technique such as flow-force coupling fractionation by using a ring-shaped channel with a rectangular cross-section. U.S. Pat. No. 4,284,498 issued to Grant et al. (DuPont de Nemours & Company) also mentions a ring-shaped channel with a rectangular cross-section.

The devices described in documents from the state of the art however pose the problem that a reproducible separation of suspended substances is not obtained, in particular when the substances are cells. This is notably revealed by retention times which differ for a same species without any variation of the separation conditions; this does not allow proper utilization of the separation, notably in the case of living cells. This is also visible in the shape of the elution peaks, which is not of a Gaussian shape.

The present inventors, in particular Pr. CARDOT, have also produced several publications in this field. They have notably improved sedimentation by flow-force fractionation, in particular for separating living human cells by using the force of gravity induced by rotation of a separation bowl. However, these devices have encountered the same problems as in the devices of the prior art. In particular, the present inventors have identified a problem of deformation of the separation volume defined by the ring-shaped channel with a rectangular cross-section. This deformation notably occurs during the tightening of the channel for putting it in place in the separation bowl.

OBJECTS OF THE INVENTION

The main object of the invention is to solve the technical problem consisting of providing a new separation device, notably a flow-force coupling fractionation device (FFF), allowing a reproducible separation of suspended substances in a liquid carrier, in particular by restoring the Gaussian shape of the elution peaks and/or by obtaining reproducible retention times.

The object of the invention is also to solve the technical problem consisting in providing a new separation device, notably an FFF device, in particular a sedimentation (gravitational field) FFF device, which allows living cells to be separated in a reproducible manner. In particular, these cells are human cells, preferably cells present in physiological liquids, in particular in blood, such as the red corpuscles of blood.

The object of the invention is also to solve the new technical problem consisting in finding a technical solution which avoids deformation of a substantially ring-shaped separation channel with a substantially rectangular section, in particular an FFF separation channel.

The object of the invention further is to solve the technical problem consisting in providing an device that may easily be disassembled for carrying out an easy cleaning, notably sterilization/decontamination, on the one hand; and on the other hand for allowing a device to be changed, in particular in order to change the properties of the separation channel for separating different substances, optionally in a different liquid carrier. In particular, this change is made necessary in the frequent case of processing different biological liquids, from different carriers, notably for avoiding contaminations.

A further object of the invention is to solve the technical problem consisting of providing a separation device affording very great flexibility in use, notably by allowing the geometrical parameters of the separation device to be rapidly changed while having a wide selection as to the separation device used.

DESCRIPTION OF THE INVENTION

Separation Device

Thus, the present invention in a first aspect describes a device for separating solutions containing suspended substances in a liquid carrier, notably within the scope of centrifugation, comprising a casing comprising a cavity defining a substantially cylindrical internal surface with a predetermined height, and at least a first actual separation channel with a substantially cylindrical annular shape and a substantially rectangular cross-section, formed by the combination of three mounting components i.e. a first mounting component with a wall portion defining at least a first side wall of said separation channel, a second mounting component including at least one recess defining a second side wall of said separation channel and the dimension of said separation channel, and a third mounting component being positioned against the second component, defining a third side wall and completing said separation channel, characterized in that it comprises at least a second channel called a counter-channel, positioned facing the first separation channel, between the first mounting component and said internal wall of the cavity of the housing.

Preferably, the first separation channel has a sufficient size in order to, in the mounted position, substantially cover said substantially cylindrical internal surface of said cavity, completely.

Very advantageously, with this, the channel and/or the counter-channel may be very rapidly assembled and/or disassembled, notably for changing the materials of the mounting components of which they consist.

Very advantageously, with this, the dimensions of different mounting components may also be changed, notably for changing the separation parameters such as the separation volume.

Advantageously, the thickness of the second mounting component defines the thickness of first separation channel; and in that the thickness of the counter-channel is substantially identical with the thickness of the first separation channel. This thickness is generally between 0.050 and 2 mm, preferably between 0.070 and 0.200 mm, such as between 0.100 and 0.175 mm, for example.

Preferably, the cross-section of the counter-channel is larger than the cross-section of the first separation channel, notably in the direction corresponding to the cylindrical wall in the mounted position.

Also preferably, the second mounting component comprising said recess is made out of a material having mechanical properties different from those of the material of the first mounting component and/or the third mounting component.

According to one embodiment, the second mounting component is made out of a material having sufficient mechanical properties so as to be substantially without creep, notably under the effect of tightening pressure.

Advantageously, the counter-channel is formed by the combination of a fourth mounting component positioned between the first mounting component and the internal wall of the casing, and comprising a second recess at least as large as the first recess, said second recess being positioned, in the mounted condition, facing the first recess, and a fifth mounting component positioned against the internal wall of said cavity of the casing.

Preferably, the second mounting component is formed from a substantially planar sheet wherein the aforementioned recess is formed by a cutout with preferably bevelled side end edges.

Preferably, the fourth mounting component is made out of a material having mechanical properties similar to or substantially identical with those of the material of the second mounting component.

Advantageously, the material of the second mounting component is partly or preferably entirely made out of at least one sterilizable material and the surface of which may be treated in order to limit adsorption, in particular a plastic material selected from the group consisting of a metallized plastic sheet such as mylar, polycarbonate, or a metal or an alloy of at least one metal, in particular a biocompatible metal such as aluminum, an stainless noble metal.

Advantageously, the other mounting components (first mounting component, third mounting component, fourth mounting component, fifth mounting component) are also made out of a sterilizable material such as defined in the paragraph above.

Preferably, the second mounting component and the fourth mounting component are identical as regards their material. This material is preferably a metallized plastic sheet such as mylar, the thickness of which, as indicated earlier, is preferably between 0.050 and 2 mm, preferably between 0.070 and 0.200 mm, such as between 0.100 and 0.175 mm, for example. Advantageously, the thickness of the fourth mounting component is larger than the thickness of the second mounting component by about 10%. For example, the thickness of the fourth mounting component is 110 µm whereas the thickness of the second mounting component is 100 µm.

The first, third, and fifth mounting component are also preferably made out of an identical material, the thickness of which is preferably between 0.050 and 2 mm, preferably between 0.070 and 0.200 m, such as between 0.100 and 0.175 mm for example. This material is preferably polycarbonate.

With the counter-channel forming device, it is possible to avoid deformation of the separation volume, defined by the hollow space of the channel during the strong tightening required for providing the seal between the three mounting components defining the separation channel. With this counter-channel forming device and also the device forming the separation channel, it is also possible to obtain an easily interchangeable assembly for example to change the materials, the dimensions, the casing, or other parameters, in order to notably change the separation parameters.

Within the scope of the uses addressed by the present invention, it is particularly advantageous if the material of the second mounting component is compatible with biological substances, in particular, notably transportable, living cells. These materials notably are those known to one skilled in the art for such uses.

Tightening Device

A preferred tightening method is described hereafter according to the invention. This tightening method is perfectly usable in other devices. Notably, the tightening forces may thereby be distributed substantially evenly over the periphery of the channel. With this device, it is also possible to achieve uniform tightening of the annular separation channel.

According to one embodiment, the device according to the present invention comprises at least one tightening member positioned inside said cavity of the casing, and with a height substantially equal to, preferably identical with, the height of said cavity of the casing, in order to rest against substantially the entire apparent surface of the third mounting component.

Advantageously, the tightening member comprises at least two distinct tightening components with a complementary trapezoidal section, having a joined contact surface with an inclined plane defined by the inclined edge of the trapezoidal section.

Preferably, the first tightening component provided for resting against the third separation component, has a toric shape with a trapezoidal section, advantageously cut into several distinct parts.

Also preferably, the second tightening component essentially has a disk shape with the external edge defining said inclined plane of the trapezoidal section provided for cooperating with the inclined plane of the trapezoidal section of the first tightening component.

It is understood that it is advantageous when the right edge of the trapezium forms the tightening working surface against the third separation component.

Inlet/outlet Device

According to a first particular embodiment, the present invention applies an inlet and/or outlet device for the liquid carrier in the separation channel, allowing the liquid carrier to be fed in through the external periphery of the separation bowl, i.e. an inlet and/or outlet duct passes through the casing, the counter channel and the first mounting component of the channel. It is quite possible to apply the present invention in a second embodiment, wherein the inlet and/or outlet device allows the liquid carrier to be fed in through the inside of the separation bowl. Devices of this type are known in the prior art. In this second embodiment, it is advantageous to provide a through-port within the tightening device to provide passage for the inlet and/or outlet duct and to allow the liquid carrier to flow in or out of the channel by having it cross the third mounting component through a port provided within this component.

According to the first embodiment which is preferred, the first mounting component comprises at least two through-ports intended to form an inlet port and an outlet port respectively, for the liquid solution to be separated in said separation channel.

According to a particular embodiment, the device according to the present invention comprises in the bulk of the casing, at least two through-housings each intended to receive at least one part for adjusting the flow seal gaskets of the inlet and outlet for said liquid solution, comprising at least one port for receiving a tightening screw itself provided with a through-port respectively used at the inlet or at the outlet for said liquid solution, at the inlet port or at the outlet port of the fifth component. The adjustment part is movably mounted in order to allow translational movement of this part along the wall of the casing. With a slide or groove system, it is possible to give a sufficient degree of freedom to the adjustment part.

Said housings are fully patentable independently to the extent that they may be adapted to the casing used as a separation bowl in order to facilitate adjustment of the inlet and outlet. The positioning of the inlet and outlet ports of the separation channel notably depends on the tightening force or pressure.

The through-housings are advantageously located at the external periphery of the casing.

The present invention has solved this technical problem by providing a mobile system for supplying the liquid to be separated, which largely simplifies the tasks of mounting the channel and the counter-channel in a casing used as a separation bowl. The problem of adjusting the inlet and the outlet is particularly encountered when the position of the inlet and outlet ports of the channel is located before tightening the whole assembly or when the applied tightening to the channel and counter-channel assembly, is not of identical force. With this, it is also possible to obtain a degree of freedom as to the length of the separation channel. With this mobile system, advantageously, a mounting method may be applied wherein the different components respectively forming the channel and the counter-channel may be set blind. The method is described in more detail in the detailed description of the invention.

Separation Apparatus

According to a second aspect, the present invention relates to a separation apparatus comprising a separation device as described earlier.

The inventors have noticed that the separation apparatuses of the state of the art do not provide an easy procedure for the mounting and/or mountings by the manipulator. Indeed, the separation device is mounted on an axis of rotation and is between two fixed portions providing support of the axis of rotation, partly of the distal end and partly of the proximal end.

Advantageously, the separation apparatus according to the invention is asymmetrical, in order to allow it to be rapidly disassembled, and it comprises a unique fixed portion for supporting an axis of rotation, said fixed portion being located between a driving device, such as a motor, for driving the separation device into rotation, around the axis of rotation, and the separation device. The device according to the present invention may be driven into rotation either around a substantially horizontal axis of rotation, or around a substantially vertical axis of rotation. A substantially horizontal axis of rotation is preferably used, notably for facilitating application, in particular the mounting and dismantling operation.

Advantageously, the apparatus substantially comprises two distinct areas, i.e. a first easily accessible area, a so-called separation area, comprising the separation device, and a second area, a so-called driving area, comprising the driving device.

This aspect of the invention is also patentable independently to the extent that by achieving an asymmetrical mounting and/or physically separating the area comprising the separation device and the area comprising the driving device, it is possible to secure any centrifuging apparatus notably as to the driving portion, while maintaining the separation portion easily accessible. This is particularly advantageous when the apparatus is asymmetrical and allows the separation bowl to be mounted/dismantled easily and very rapidly, in particular the separation device according to the present invention.

Technical difficulties for achieving an asymmetrical centrifuging apparatus reside in the fact that it was hitherto preferable to house the separation device between two fixed portions in order to achieve good stability during the rotation. On the other hand, the prior devices are generally welded on the rotary shaft so that the device is stable and secured during rotation. However, the devices from the prior art do not allow (or only with difficulty) one skilled in the art to change the characteristics of the separation bowl and/or the separation channel.

Advantageously, the second driving area is located below the first area. With this, it is possible to maintain accessibility through the front of the high portion, for handling the separation device and the low portion, in order to perform a maintenance operation on the driving means.

According to another aspect of the present invention, the separation device or the apparatus as described earlier is used for separating suspended particles in a liquid carrier, in particular by centrifugation, preferably by a flow-force fractionation technique called FFF, in particular, living cells, in particular, living cells of human origin.

Advantageously, according to a first embodiment, the suspended particles are colloids, for example titanium dioxide.

Advantageously, according to a second more preferable embodiment, the suspended particles are living cells, in particular stem cells. Hitherto, such a separation was not possible with the system described in the prior art as good reproducibility of the separation could not be achieved.

For example, the living cells to be separated are living cells selected from the group consisting of red corpuscles, avian stem cells, neural stem cells, precursor cells in gliomas, precursor cells in neuroblastomas, glia cells of cell lines. With the present invention, other suspended biological molecules may also be separated, for example proteins, such as antibodies, or amino acids, such as a DNA, a RNA, a virus. Advantageously, the substances to be separated may be of human origin.

The device according to the present invention therefore allows the FFF technique to be adapted to the separation of living biological cells, and notably transplantable cells.

With the device according to the present invention, it is possible to identify new cells, which represents considerable progress in human and animal medical applications, cosmetological and industrial applications. With the device according to the present invention, it is also possible to do without the absence and/or ignorance of biological markers present in the cells.

In particular, it should be noted that Pr. CARDOT and his team have produced many publications on applying the FFF technique, through which all the uses of the device according to the present invention may be known. By using the device according to the present invention in applications known to one skilled in the FFF art, it is possible to obtain quite unexpected results, notably by the reproducibility of the separations, as well as by the reduced separation time.

The invention will now be described in more detail with reference to the figures.

Other objects, features and advantages of the invention will become clearly apparent to one skilled in the art upon reading the explanatory description which is made with reference to the figures which are only given by way of illustration and which may by no means limit the scope of the invention.

The figures are an integral part of the present invention and any feature appearing to be novel relatively to any state of the prior art from the description taken as a whole, including the figures, is an integral part of the invention in its function and in its generality.

DESCRIPTION OF THE FIGURES

FIG. 1 in particular shows an exemplary device 1 for separating solutions containing suspended substances in a liquid carrier, notably within the scope of centrifugation, comprising a casing 100 comprising a cavity 110 defining a substantially cylindrical internal surface 120 with a predetermined height, i.e. generally between 1 and 15 cm although this is not limiting.

Figure 1:
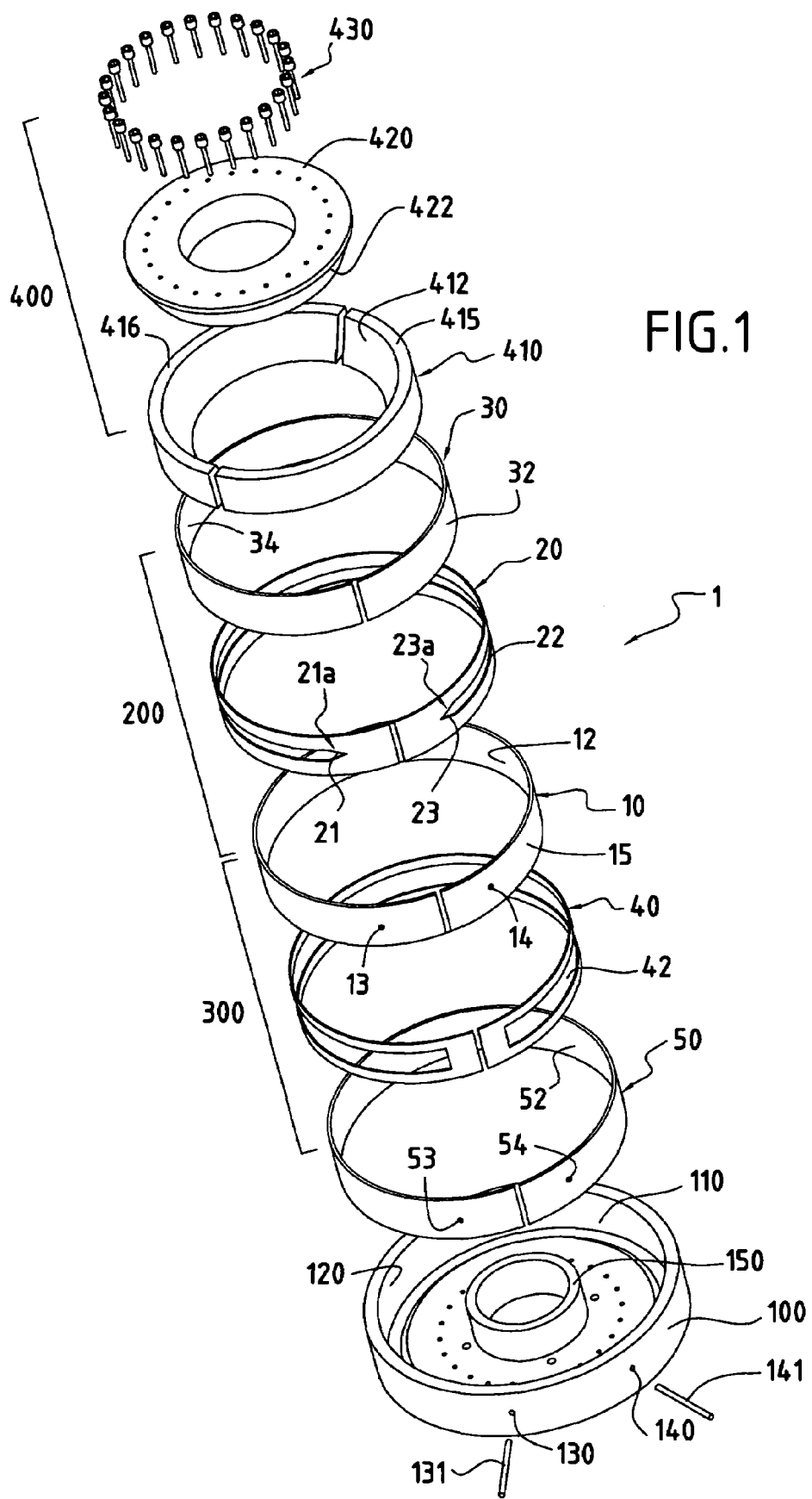
FIG. 1 illustrates an exploded perspective view of the entire components of the separation device according to the invention, including the tightening device.

Casing:

The casing 100 comprises a positioning means 150 such as a central through-port for letting through the casing 100 or for fixing it on a rotary drive shaft 702 of said casing 100 and at least a first separation channel 200. Advantageously, the positioning means 150 is adapted to receive a rotary gasket forming device, allowing the liquid carrier to flow in and/or flow out, through the inlet 131 and/or outlet 141 ducts.

Separation Channel:

The first separation channel 200 itself with a substantially cylindrical annular shape and with a substantially rectangular cross-section, is formed by the combination of three mounting components with a sufficient size in order to, in the mounted position, cover substantially completely said substantially cylindrical internal surface 120 of said cavity, i.e. a first mounting component 10 with a wall portion 12 defining at least a first side wall of said separation channel 200, a second mounting component 20 including at least a through-recess 22 defining a second side wall of said separation channel 200 and the dimension of said separation channel 200, and a third mounting component 30 being positioned against the second component 20, defining a third side wall 32 and completing said separation channel 200.

According to the invention, this device is characterized in that it comprises at least a second channel 300, a so-called counter-channel, positioned facing the first separation channel 200, between the first mounting component 10 and said internal wall 120 of the cavity 110 of the casing 100.

Counter-channel:

The counter-channel 300 is formed by the combination of:

a fourth mounting component 40 positioned between the first mounting component 10 and the internal wall 120 of the casing 100 and comprising a second recess 42 at least as large as the first through-recess 22, said second recess 42 being positioned, in the assembled condition, facing the first recess 22, and a fifth mounting component 50 positioned against the internal wall 120 of said cavity 110 of casing 100. The device comprises at least a tightening member 400 positioned inside said cavity 110 of the casing 100 and having a height substantially equal to, preferably identical with, the height of said cavity 110 of the casing 100, in order to substantially rest against the entire apparent surface 34 of the third mounting component.

Tightening Member:

According to an advantageous embodiment, the tightening member 400 comprises at least two distinct tightening components (410,420) with a complementary trapezoidal section having a joined contact surface with an inclined plane.

Advantageously, the first tightening component 410, provided for resting against the third separation component 30, has a hollow cylindrical shape with a trapezoidal section, cut up into several distinct parts, for example into two distinct parts (415,416), even three distinct parts in order to distribute the tightening compression force as best as possible. It is understood that the vertical external edge 414 of the first tightening component 410 forms the tightening working surface against the apparent surface 34 of the third mounting component 30.

In particular, the second tightening component 420 essentially has a disc shape with the external edge 422 defining said inclined plane of the trapezoidal section, provided for cooperating with the inclined plane of the trapezoidal section of the first tightening component 410, formed by the inner edge 412. Both tightening components (410,420) are maintained integral with the casing 100 by supporting means 430, such as screws known to one skilled in the art for providing an even distribution of exerted forces during the tightening of one tightening component, such as the second tightening component 420. This is quite advantageous so as not to deform the assembly separation channel 200 against channel 300.

Through-ports:

Advantageously, the first mounting component 10 comprises at least two through-ports 13, 14 intended to respectively form an inlet port 13 and an outlet port 14 for the liquid solution to be separated in said separation channel 200. The fifth mounting component 50 also includes the same ports 53 and 54. The casing 100 also includes two through-holes (130, 140) for providing the inlet and outlet for the liquid solution to be separated in said separation channel 200. With the through-ports (13, 14, 53, 54, 130, and 140) it is possible to introduce means for feeding in (131) and feeding out (141) the liquid carrier comprising substances to be separated. For example, these means are tubes for chromatography, such as HPLC tubes. Mounting these tubes is carried out sealably so that the liquid carrier as well the substances to be separated which must pass into the separation channel, are not found in the recess 42 of the counter-channel.

The casing 100 for example is of an effective internal diameter of the separation cavity 110, of 30 cm. The diameters of the casings 100 will generally be between 5 and 50 cm, preferably between 8 and 15 cm and will vary according to the desired separation. The lower the mass of the casing, the higher are the potential rotational velocities.

Figure 2:
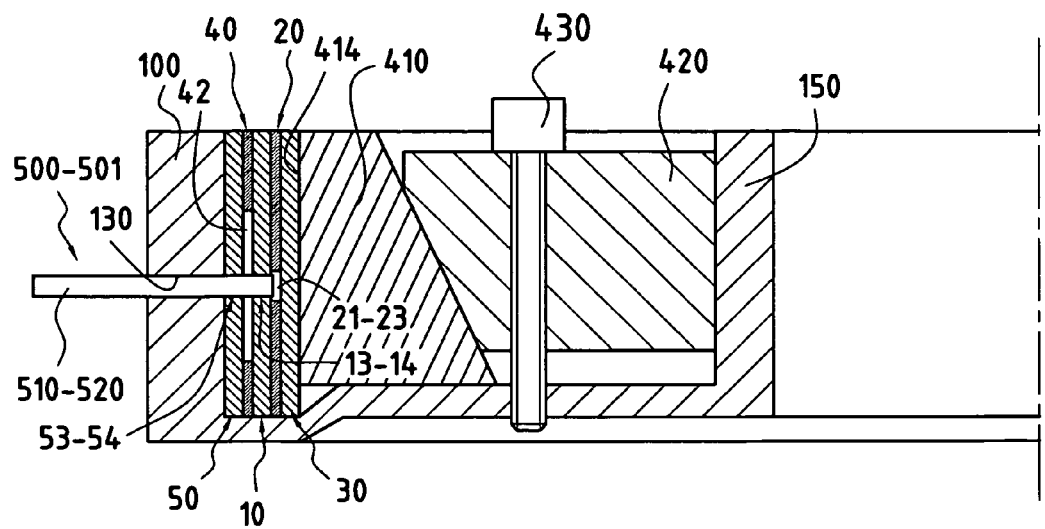
FIG. 2 illustrates a sectional view of the device according to the present invention including the tightening device mounted in its position of use.

FIG. 2 shows a cross-section of the device according to FIG. 1 in the operating tightened position. It is notably seen that a component 500 to be used at inlet 510 or a component 501 to be used at outlet 520 of the liquid solution to be separated, may be introduced into the inlet 130 or outlet 140 ports. Component 500, 501 is advantageously positioned facing the beveled end of the recess defining the separation channel 200, by being substantially tangential to the internal surface 12 of the first component 10. Elements 500, 501 penetrate into the fifth mounting component 50 via through-ports 53, 54 and pass through the counter-channel in the recessed portion 46.

Figure 3:
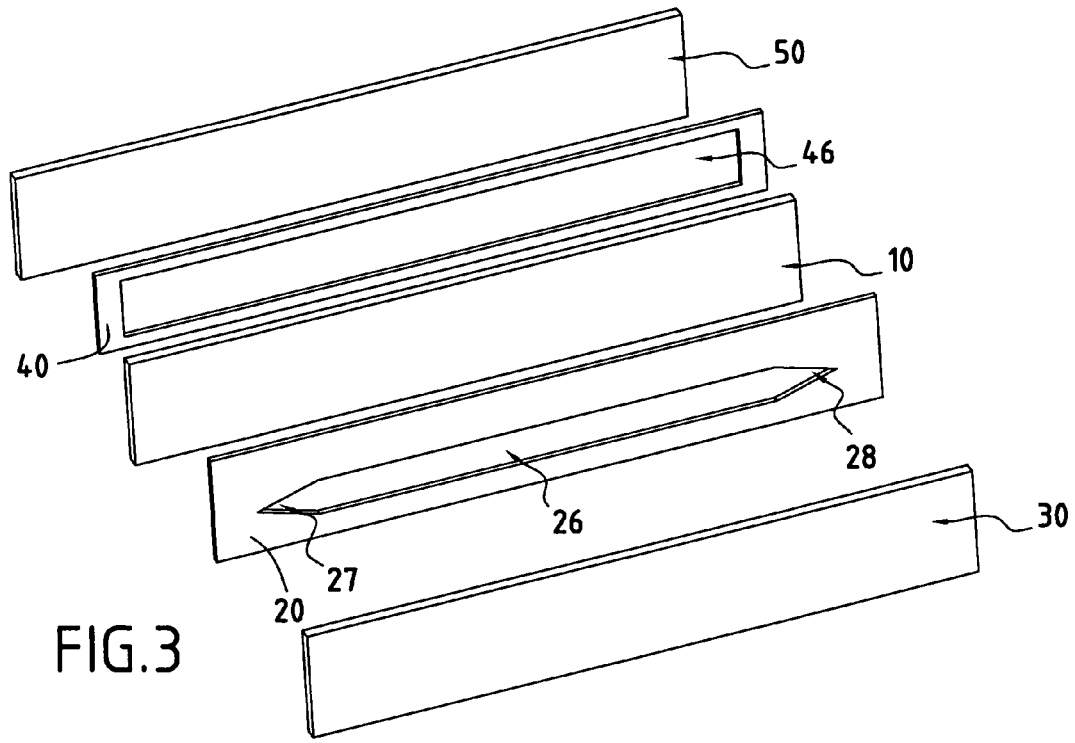
FIG. 3 illustrates an exploded perspective view of the channel and of the counter-channel.

FIG. 3 illustrates an exploded perspective view of the separation channel 200 counter-channel 300 assembly. The mounting components 10, 30, 50 are formed by strips or sheets with a substantially parallelepipedous external shape, the section being substantially rectangular and they generally have dimensions of about: width=0.5-15 cm, preferably from 0.7 to 2 cm, length=10 cm-1 m, preferably from 20 cm to 80 cm, thickness=0.010-20 mm, preferably from 0.050 to 0.200 mm, still preferably from 0.070 to 0.0120 mm.

The second mounting component 20 is substantially parallelepipedous and comprises a substantially parallelepipedous through-recess 26 on the greater part of its dimension but also includes a bevel at the distal portions 27 and 28. The fourth mounting component 40 which is substantially parallelepipedous also comprises a substantially parallelepipedous recess 46. Recess 46 has a size preferably slightly larger than that of recess 26, notably in the direction corresponding to the cylindrical wall in the mounted position. Recess 46 generally has the dimensions:

width=0.5-15 cm, preferably from 0.5 to 2 cm, length=10 cm-1 m, thickness=0.010-20 mm, preferably from 0.050 to 0.200 mm, still preferably from 0.070 to 0.0120 mm, and recess 26 generally has dimensions: width=0.5-15 cm, preferably from 0.5 to 2 cm, length=10 cm-1m, thickness=0.010-20 mm, preferably from 0.050 to 0.200 mm, still preferably from 0.070 to 0.0120 mm. The bevel forming the end of the separation channel generally is of a length from 1 to 7 cm.

The mounting components are positioned so as to have an annular shape in contact with the internal surface of the casing 100 according to FIG. 1. The mounting procedure is the following, made with reference to FIG. 1:

a) First Mounting Step for Locating the Length of the Provided Recesses

The largest surface of the fifth mounting component 50 is positioned into contact with the internal surface 120 of the casing 100. The fourth mounting component 40 (still not comprising recess 42) is positioned in an annular way against the internal surface 52 of the fifth mounting component 50. Then, the first mounting component 10 is positioned in an annular way into contact with the first mounting component 40. The second mounting component 20 (still not comprising recess 22) is mounted in an annular way into contact against the internal surface 12 of the first mounting component 10. Finally, the third component 30 is positioned in an annular way in order to place surface 32 into contact with the second mounting component 20. These steps are performed blindly, i.e. without any particular precaution as to the position of the different components, with the exception of the second and fourth mounting components (20, 40) which should positioned so that the end of the parallelepipedous strip (20, 40) is positioned between the inlet 130 and the outlet 140 of the casing 100.

b) Second Tightening Step.

Tightening is performed very progressively in order to obtain a tightening force of the order of 10N for example. The positioning of the inlet port 130 and the outlet port 140 on the entire mounting components 10, 20, 30, and 40 is identified with localization means.

c) Third Step for Dismantling and Cutting out the Recesses.

The entire mounting components 10, 20, 30, 40, and 50 are removed. The cutting of the second mounting component 20 and of the fourth mounting component 40 is achieved advantageously in order to define the recess 22 of the second mounting component and the recess 42 of the fourth mounting component. The recess 42 of the fourth mounting component is of a length slightly larger than the recess 22 of the second mounting component. The recess 22 of the second mounting component advantageously comprises at the proximal 21 and distal 23 end portions, a bevel 21a, 23a, the end of which corresponds to the location of the positioning of the inlet port 130 and the outlet port 140. Because of the recess 42 of the fourth mounting component 40, the means for locating the inlet port 130 and the outlet port 140 should no longer be apparent on the fourth mounting component 40.

d) Fourth Mounting Step After Cutting out the Recesses.

One proceeds identically as with the first mounting step, i.e. with positioning the mounting components 10, 20, 30, 40, and 50 within the casing 100.

e) Fifth Tightening Step.

Next, the first tightening component 410 is placed between the means 150 for positioning the casing 100 on a rotary shaft and the third mounting component 30. The second tightening component 420 is then placed against the first tightening component 410 and the positioning means 150. One then proceeds with securing the second tightening component 420 with the supporting means 430 onto the casing 100.

One then proceeds with introducing the means for feeding in 131 and feeding out 141 the liquid carrier comprising the separated substances, within the inlet 130 and outlet 140 ports of the casing 100. These feeding-in means 131 and feeding-out means 140 are positioned tangentially to the internal surface 12 of the first mounting component 10 and they must be sealed respectively between their external edge and the inlet 13 or outlet 14 through-port. This position may be slightly different in order to vary the position for introducing the liquid carrier comprising the substances to be separated within the separation channel 200. The positioning of the feeding-in 130 and feeding-out means 140 within the casing 100 is provided by an inlet port 73 and an outlet PCT port 74, preferably via the mobile component 70 (FIG. 5) comprising a through-port 72. The mobile component 70 is maintained in position by a positioning component 81, for example a screw (in the screwed position), via the positioning port 71.

Advantageously, the second mounting component 20 is formed from a substantially planar strip or sheet wherein the aforementioned recess is formed by a cut-out with bevelled 21a, 23a side end 21, 23 edges.

Figure 4:
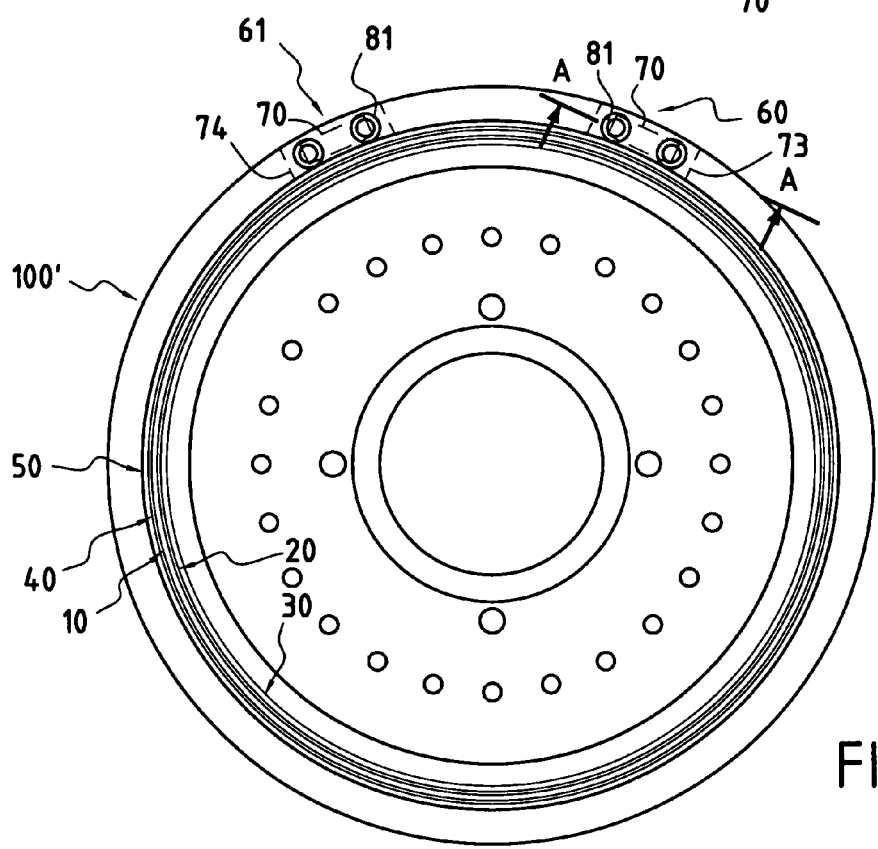
FIG. 4 illustrates a top view of the separation device.

FIG. 4 illustrates a top view of the component forming the separation device 1 according to the present invention without the tightening component. The casing 100', the first mounting component 10, the second mounting component 20, the third mounting component 30, the fourth mounting component 40 and the fifth mounting component 50 may be seen. The casing 100' is independently patentable because of means 60 (through-housing described hereafter). This assembly is notably advantageous if the feeding-in and/or feeding-out of the carrier liquid is performed through the external periphery of the separation bold, i.e. as shown in FIG. 1.

Through-housing of the Casing

Figure 5B:
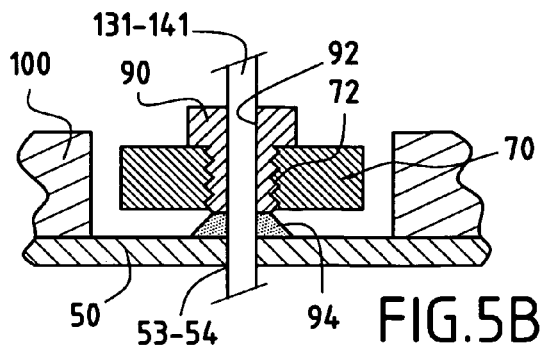
FIGS. 5a and 5b respectively illustrate a section AA and a section BB of the casing having independently patentable housing components according to the present invention.
Figure 5A:
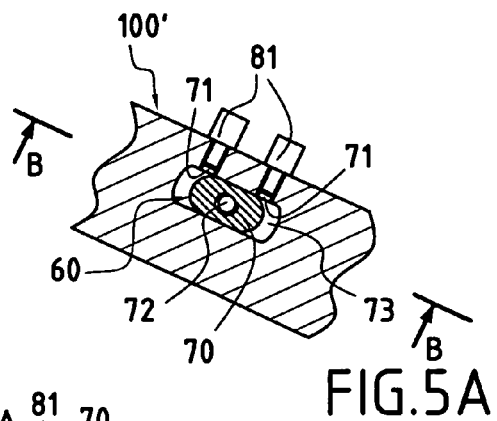

FIG. 5a illustrates a section AA (along an axis parallel to the axis of the cylinder formed by the casing) of the independently patentable casing 100' according to the present invention. Casing 100' comprises at least two through-housings 60, 61 each intended to receive at least one part 70 for adjusting the flow seal gaskets of the inlet and outlet for said liquid solution, comprising at least a through-port 72 for receiving a tightening screw 90 itself provided with a through-port respectively to be used at the inlet or outlet for said liquid solution at the input 13 or output 14 port of the first component 10. The adjusting part 70 is maintained in position with at least one positioning component 81, such as a screw, via at least a positioning port 71.

FIG. 5b illustrates a section BB (along an axis perpendicular to the axis formed by the cylinder of the casing) of the through-housing 60,61. The tightening screw 90 intended to be housed in the receiving through-port 72 includes a port 92 allowing inlet 131 or outlet 141 ducts to be introduced. The seal is provided at the inlet 53 or outlet 54 port of the second mounting component 50 by sealing means 94, preferably a conical gasket. The sealing means 94 is preferably in contact with the external wall of the fifth component 50 and comprises a port for receiving the inlet 131 or outlet 141 duct. A good seal is provided by the pressure exerted by the tightening screw 90 on the sealing means 94.

Asymmetrical Mounting of the Separation Device

Figure 6:
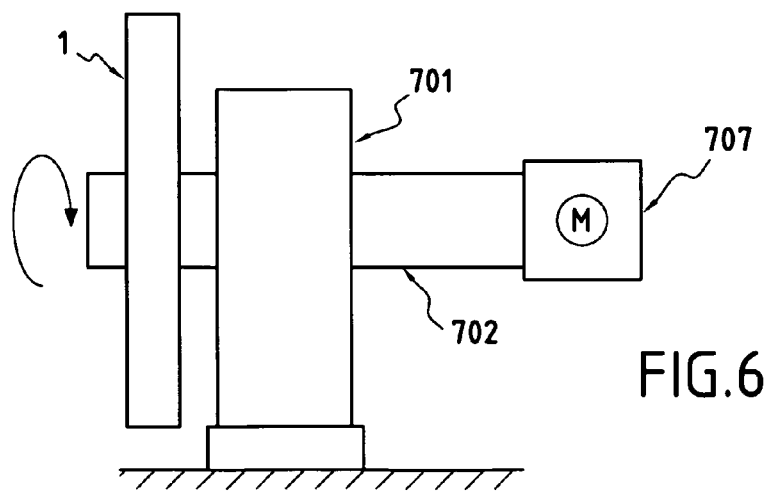
FIG. 6 illustrates a diagram of an asymmetrical separation apparatus, comprising the independently patentable separation device according to the present invention.

FIG. 6 illustrates a schematic view of the position of the separation device 1 mounted asymmetrically. The separation device 1 is positioned on the rotary drive shaft 702. The fixed portion 701 providing support of the rotary shaft 702 is only present between the separation device 1 and the means 707 for driving the shaft 702.

Separation Apparatus

Figure 7:
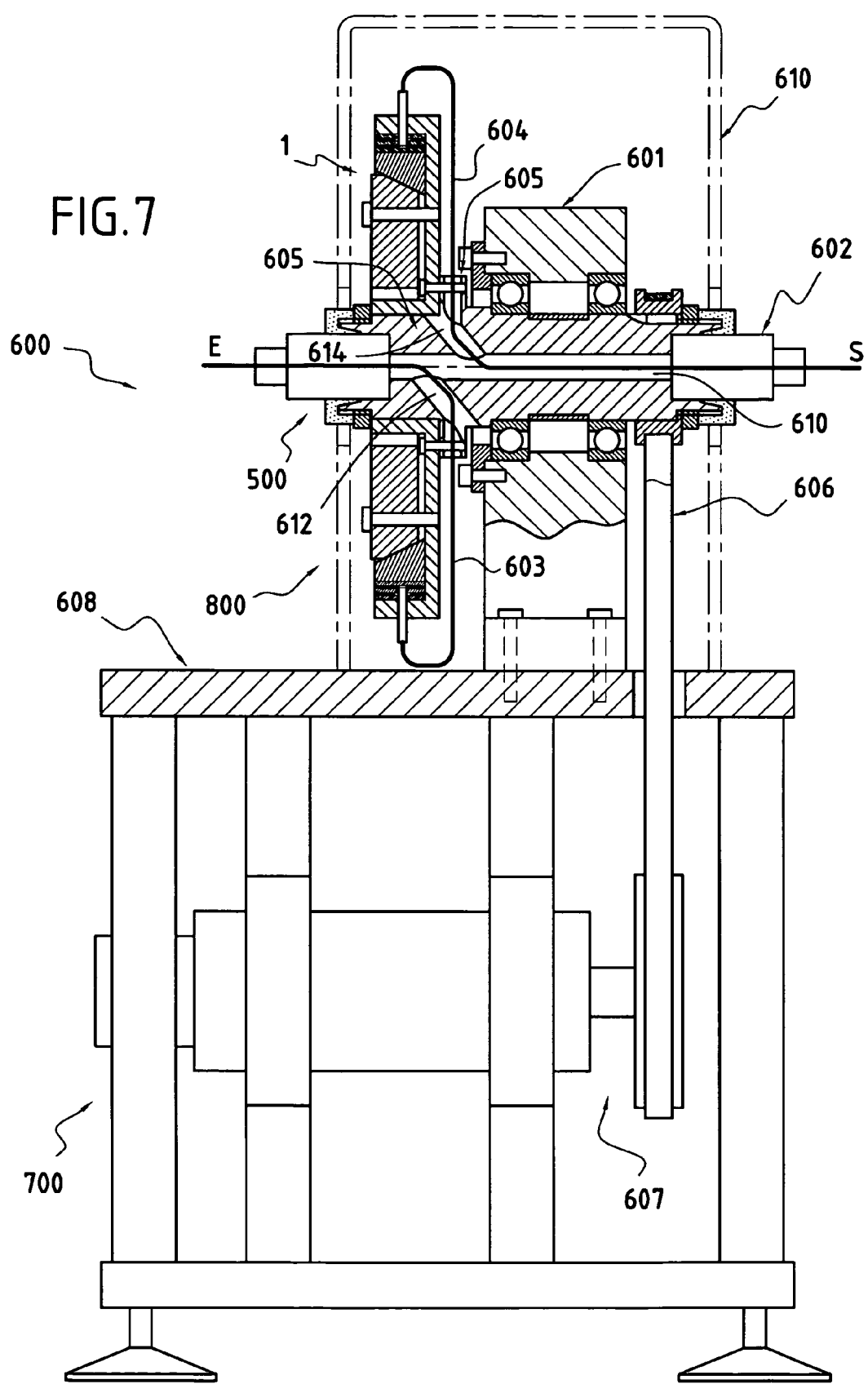
FIG. 7 illustrates a longitudinal section of an asymmetrical separation apparatus, comprising the separation device according to the present invention.

FIG. 7 illustrates a longitudinal section of the asymmetrical separation apparatus 600 comprising a separation device 1, according to the present invention. This device shows a fixed portion 601 comprising a recess for receiving a rotary shaft 602. The rotary shaft 602 also comprises a recess for passing through feeding-in 603 and feeding-out 604 means such as inlet and outlet tubes for the liquid carrier comprising the substances to be separated. Preferably these tubes are flexible tubes usually used in the field of analytical chemistry for feeding in and out liquid carrier comprising substances to be separated, and for example, they are flexible tubes used for HPLC separation, with an internal duct diameter of about 163 µm for example. By mounting these inlet and outlet ducts in this way, they cannot be entangled during the rotation. Preferably, the recess 610 of the rotary shaft 602 is a through-recess along the axis of rotation. Recess 610 is also preferably of a cylindrical shape. The rotary shaft 602 advantageously comprises at least a radial recess 612,614 extending from recess 610 to the periphery of the axis of rotation 602, allowing the inlet 603 and outlet 604 ducts to pass from a position substantially parallel to the axis of rotation, to the outside of the rotary shaft 602 by radially exiting the body of the rotary shaft in order to be inserted onto the outside of the separation device 1. The axis of rotation 602 comprises means 605 for securing the separation device 1 according to the present invention. This securing means 605 advantageously is a cylindrical protrusion of the axis of rotation 602 for example comprising screw threads for securing the separation device 1 thereon, for example with screws or allowing a bolt-nut system to be installed thereon. Advantageously these means are easy to mount and/or dismantle so as to allow the user to easily mount and/or dismantle the separation device 1 according to the present invention from the axis of rotation 602. In particular, the recess 612,614 of the rotary shaft 602 allowing the inlet 603 and outlet 604 ducts to be introduced or extracted radially, is comprised in the securing means 605. Advantageously, with the rotary shaft 602, it is possible to receive at least a rotary gasket forming device 620,630. The rotary gasket forming device 620,630 provides a sealed junction between a fixed inlet duct 621 and a rotary inlet duct 622 or between a fixed outlet duct 631 and a rotary outlet duct 632. Advantageously, the axis of rotation is driven by means for transferring a rotary movement 606, which is a belt for example. The transfer means 606 is connected to a rotation means 607, such as a motor.

According to a particular embodiment for securing the separation apparatus, the axis of rotation 602 on which is mounted the separation device 1 according to the present invention, is contained in a protective casing 610.

According to a particular embodiment, the rotation means 607 is physically separated from the so-called separation area 800 comprising the separation device 1, the axis of rotation 602 and the fixed portion 601. Preferably, the rotation means is located below the separation apparatus 600. More preferably, the rotation means 607 is located under a planar horizontal surface 608 and the separation apparatus 600 is positioned above the surface 608. With this mounting, the manipulators may easily intervene on the so-called separation portion comprising the separation device 1, and the driving mechanical portion 700 comprising the driving means 607 is accessible for maintenance without any risks of damaging the so-called separation portion.

Other objects, features and advantages of the invention will become clearly apparent to one skilled in the art upon reading the explanatory description which is made with reference to examples which are only given by way of illustration and which may by no means limit the scope of the invention.

The examples are an integral part of the present invention and any feature appearing to be novel relatively to any state of the prior art, from the description taken as a whole, including the examples, is an integral part of the invention in its function and in its generality.

Thus, each example has a general scope.

On the other hand, in the examples, all the percentages are given by weight, unless specified otherwise, and temperature is room temperature or is expressed in degrees Celsius unless specified otherwise, and pressure is atmospheric pressure, unless specified otherwise.

EXAMPLES

Example 1

Example of a Procedure for Checking the Volume of the Separation Channel of the Device According to the Present Invention The following procedure is carried out in order to check the volume of the separation channel, notably to know whether the separation channel has an annular geometrical shape with a rectangular section which has not undergone any deformation during the tightening of the components forming the channel and the counter-channel.

Once the dimensions of the separation channel have been selected by cut-out from a mylar sheet and the dimensions of the counter-channel have been selected from a mylar sheet, both of these sheets are inserted as indicated in reference with FIGS. 1-7 in order to form the second and fourth mounting components against polystyrene sheets which form the first, third and fifth mounting components.

The volume of the separation channel is checked by injecting acetone via a HPLC injector.

When the separation channel is properly fixed, notably without any deformation, the elution volume should correspond to the geometrical dead volume of the channel and the typical profile should be monomodal of the Gaussian type. If necessary the tightening should be resumed.

Figure 8:
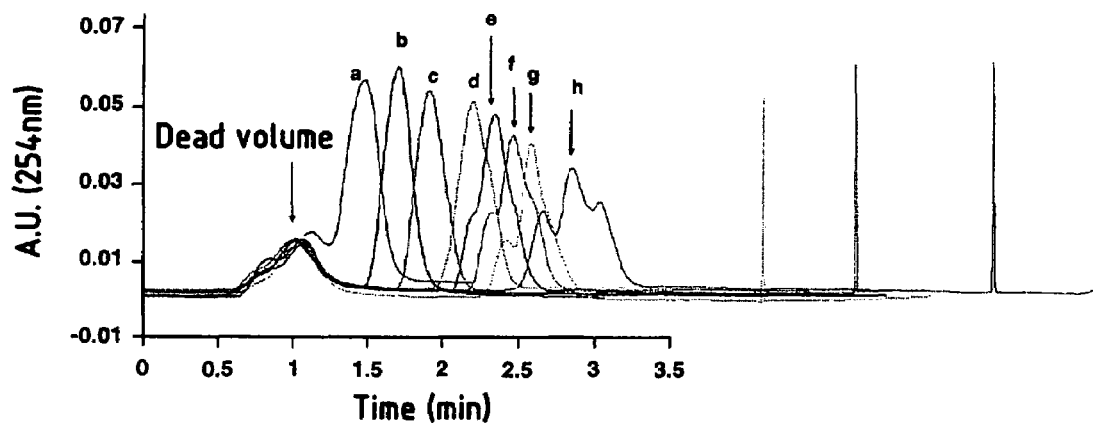
FIG. 8 illustrates the time course of detection of latex beads versus time in order to check for proper tightening of the channel/counter-channel assembly.

Monodisperse latex beads are used for checking the dead volume with a particle diameter of 7 µm, for example when the separation channel has a thickness of 80 µm. The beads are eluted by using the steric-hyperlayer mode. When the monodisperse latex beads are eluted in a channel which is not properly tightened, the elution profile appears to be monomodal for high retention ratios (FIG. 8, a, b, c, d). When the external field is increased in strength (increase in the speed of rotation) the elution profile is completely perturbed and appears to be multimodal (FIG. 8, e, f, g, h). Consequently, a reciprocal movement is performed in the tightening procedure in order to reach the desired elution profile. It may be noted that the dead volume of the liquid carrier comprising the surfactant has a remarkable monomodal Gaussian profile. When the measured dead volumes are consistent with the theoretical volume of a channel with annular geometry and with rectangular section, it is considered that the channel is properly tightened.

With the system according to the present invention, good reproducibility of the retention times and intensity of the peaks may be obtained.

Figure 9:
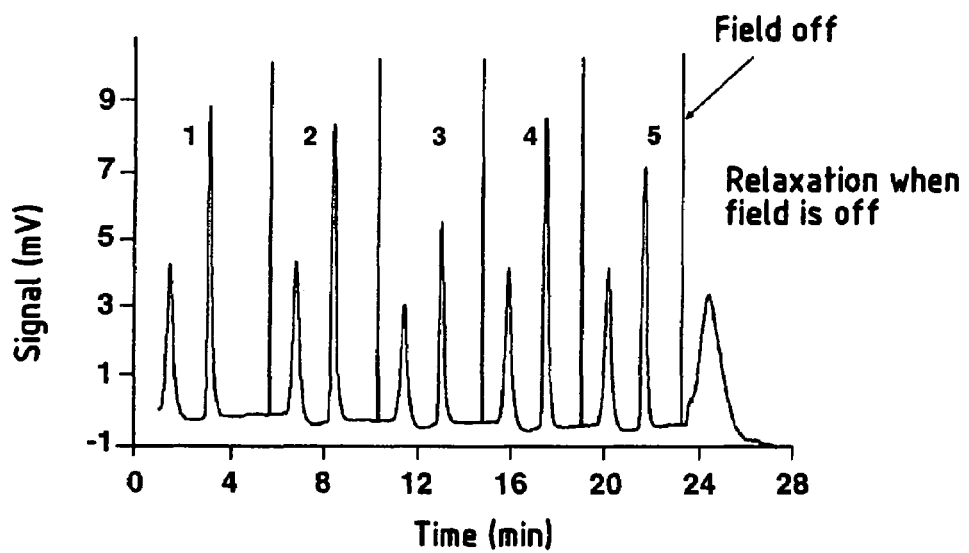
FIG. 9 illustrates the reproducibility of the retention times, for example of latex beads.

For example when the separation channel has a length of 78.4 cm, elution of latex beads with a diameter of 7 μm is carried out in less than 4 minutes with a retention ratio of 0.5 as shown in FIG. 9 where 5 repeated injections of the eluent containing the latex beads were carried out.

For example, if the first, third and fifth mounting components are made in polycarbonate polymer with a thickness of 2.0 mm, if the second and fourth mounting components are made in a mylar sheet with a thickness of 250 μm respectively having a recess with dimensions: 78.5×1×0.0250 cm and 78.5×1×0.0275 cm, the associated dead volume is 2.11±0.09 mL measured with a 0.1% (w/w.) sodium benzoate aqueous solution.

Example 2

Cell Sorting of Cells with the Device According to the Present Invention

It is possible to separate cells under the following conditions:

the separation channel is made with two polystyrene strips of dimensions 870×30×2 mm, separated by a Mylar® strip in which the channel has been cut out. The dimensions of the channel were 685×10×0.125 mm with V-shaped ends of 70 mm.

The dead volume (volume of the channel+tube connection+injection system+detection system) was 960±5 μL. The dead volume was calculated after injection of the unretained compound (water with 0.1 g/L of benzoic acid) and the retention time was determined by UV detection at 254 nm (the wavelength is adapted according to the cells to be detected). The PEEK® inlet and outlet tubes with ID of 0.254 mm were directly flush with the accumulation wall. The strips of polystyrenes and mylar were fixed in the centrifugation casing as described with reference to the figures. The distance axis of rotation-channel was measured to be 13.8 cm. The sedimentation field is expressed in gravity units, 1 g=980 cm/s$^2$, calculated by using the rotational velocity with the radius described above. The sterile mobile phase was pumped with a conventional chromatography pump used for HPLC.

The whole was controlled by a pilot unit known to one skilled in the art for providing control of the centrifugal rotational velocity.

The samples were injected after mounting the whole of the separation device and after it had been put into rotation. The external gravitational field was between 30 and 60 g. The flow rate of the mobile phase was from 0.4 to 1.0 mL per minute. The injection volume was 100 μL of injected cells at a flow rate of 0.6 mL/min. The mobile phase was a sterile PBS phase at pH 7.4 added with 1% of penicillin/streptomycin and 1% of fungizone. The multigravitational external field was 40.00±0.03 g and the detection spectrophotometer was adjusted to a wavelength of 254 nm.

Fractions of the cells were collected. This allowed the eluted cells to be characterized by immunocytochemical analysis according to conventional methods known to one skilled in the art.

Two cell populations, with different functional and expression properties (proliferation and network formation), were able to be individualized by this FFF sorting method. This therefore opens extremely interesting perspectives for investigating properties of these cells and for using them.

Example 3

Another Example of Separation of a Suspension of a Cell Line with the Device According to the Present Invention The elution conditions were those of example 2 except for the following:

dimensions of the channel: 780×10×0.125 mm;
dimensions of the counter-channel: 780×10×0.135 mm
injection of 100 microliters of cells (10$^7$ cells /mL);
flow rate: 0.60 mL/min;
mobile phase: sterile. PBS, pH=7.4 with 0.1% (w/v) BSA;
multi-gravitational external field=40.00 g±0.01 g;
detection by spectrophotometry at λ=254 nm.

Thus, it was possible to obtain different fractions of a cell line, so that present cells at different maturation stages could be separated.

What is claimed is:

1. A device (1) for separating solutions containing suspended substances in a liquid carrier comprising a casing (100) comprising a cavity (110) defining a substantially cylindrical internal wall (120) with a predetermined height, and at least an actual first separation channel (200) with an annular substantially cylindrical shape with a substantially rectangular cross-section, formed by the combination of three mounting components: a first mounting component (10), a wall portion of which defines at least a first side wall of said separation channel, a second mounting component (20) including at least a recess (22) defining a second side wall of said separation channel (200) and the dimension of said separation channel (200), and a third mounting component (30) being positioned against the second component, defining a third side wall and completing said separation channel (200), said device comprising at least a second channel called counter-channel (300), positioned facing the first separation channel (200), between the first mounting component (10) and said internal wall (120) of the cavity (110) of the casing (100).

2. The device according to claim 1, wherein the thickness of the second mounting component (20) defines the thickness of the first separation channel (200); and wherein the thickness of the counter-channel (300) is substantially identical with the thickness of the first separation channel (200).

3. The device according to claim 1, wherein the cross-section of the counter-channel (300) is larger than the cross-section of the first separation channel (200).

4. The device according to claim 1, wherein the second mounting component (20) comprising said recess (22) is made out of a material having mechanical properties different from those of the material of the first mounting component (10) and/or of the third mounting component (30).

5. The device according to claim 1 wherein the second mounting component (20) is made out of a material having sufficient mechanical properties so as to be essentially without creep.

6. The device according to claim 1 wherein the counter-channel is formed by the combination of a fourth mounting component (40) positioned between the first mounting component (10) and the internal wall (120) of the casing (100) and comprising a second recess (42) at least as large as the first recess (22), said second recess (42) being positioned in the mounted state, facing the first recess, and a fifth mounting component (50) positioned against the internal wall (120) of said cavity (110) of the casing (100).

7. The device according to claim 1 wherein the fourth mounting component (40) is made out of a material having mechanical properties similar to or substantially identical with those of the material of the second mounting component (20).

8. The device according to claim 1 wherein the material of the second mounting component (20) is compatible with biological substances.

9. The device according to claim 8, wherein the material of the second mounting component (20) is compatible with transportable, living cells.

10. The device according to claim 1, wherein the entire mounting components (10,20,30,40,50) are compatible with biological substances.

11. The device according to claim 1, wherein the material of the second mounting component (20) is made out at least partly or totally of a sterilizable material and the surface of which may be treated for limiting adsorption.

12. The device according to claim 11, wherein the second mounting component (20) is made out of a plastic material selected from the group consisting of a metallized plastic sheet mylar and polycarbonate, or of a metal material selected from the group consisting of an alloy of at least one metal, a biocompatible metal, aluminium, and a stainless noble metal.

13. The device according to claim 1, wherein said device comprises at least one tightening member (400) positioned inside said cavity (110) of the casing (100), and having a height substantially equal to or identical with, the height of said cavity (110) of the casing (100), in order to rest against substantially the entire apparent surface of the third mounting component (30).

14. The device according to claim 13, wherein the tightening member (400) comprises at least two distinct tightening components. (410, 420) with a complementary trapezoidal section having a joined contact surface (422,412) with a inclined plane defined by the inclined edge of the trapezium.

15. The device according to claim 14, wherein the first tightening component (410), provided for resting against the third separation component (30), has a hollow cylindrical shape with a trapezoidal section (412).

16. The device according to claim 14, wherein the second tightening component (420) essentially has a disc shape, the external edge of which (422) defines said inclined plane of the trapezoidal section provided for cooperating with the inclined plane (412) of the trapezoidal section of the first tightening component (410).

17. The device according to claim 1, wherein the first mounting component (10) comprises at least two through-ports (13,14) intended to respectively form an inlet port (13) and an outlet port (14) for the liquid solution to be separated in said separation channel (200).

18. The device according to claim 1, the second mounting component (20) is formed from an essentially planar sheet in which the aforementioned recess (22) is formed by cut-out with bevelled side end edges (21a, 23a).

19. The device according to claim 17, wherein the device comprises in the bulk of the casing (100) at least two through-housings (130,140) each intended to receive at least one part (70) for adjusting the flow seal gaskets (94) of the inlet and outlet for said liquid solution, comprising at least a receiving port (72) of a tightening screw (90) itself provided with a through-port (92) respectively to be used at the inlet (131) or at the outlet (141) for said liquid solution at the inlet port (53) or the outlet port (54) of the fifth component (50).

20. A centrifugal separation apparatus (600) comprising a separation device (1) of claim 1.

21. The apparatus according to claim 20, wherein the apparatus (600) is asymmetrical, in order to allow rapid dismantling, and comprises a unique fixed part (701) for supporting an axis of rotation (702), said fixed part (701) being located between a driving device (707), in order to drive the device (1) into rotation around the axis of rotation (702), and the device (1).

22. The centrifugal separation apparatus according to claim 20, wherein the apparatus substantially comprises two distinct areas: a first easily accessible area, so-called separation area, comprising the separation device (1), and a second driving area (700) comprising the driving device (607).

23. The separation apparatus according to claim 22, wherein the second driving area (700) is located below the first separation area (800).

24. A method for separating suspended particles in a liquid carrier by centrifugation comprising using the device (1) as defined according to claim 1.

25. The method of claim 24 for separating by a flow-force fractionation technique called FFF.

26. The method according to claim 24, wherein the particles are living cells.

27. The use according to claim 26, wherein the living cells are stem cells.

28. The method according to claim 24, wherein the particles are living cells selected from the group consisting of avian stem cells, neural stem cells, precursor cells in gliomas, precursor cells in neuroblastomas, glial cells of cell lines, proteins, nucleic acids, and viruses.

* * * * *